United States Patent [19]
Matsuura et al.

[11] Patent Number: 5,407,667
[45] Date of Patent: Apr. 18, 1995

[54] COMPOSITION CONTAINING INCLUSION COMPLEX OF GLUTATHIONE AND A OR β-CYCLODEXTRINE

[75] Inventors: Ichiro Matsuura, Toyko; Yasuhisa Kimura, Funabashi; Yasuo Sakai, Ibaraki; Norio Nakatsuji, Mishima, all of Japan

[73] Assignee: Kyowa Hakko Kogyo Co., Ltd., Tokyo, Japan

[21] Appl. No.: 84,437

[22] Filed: Jul. 1, 1993

Related U.S. Application Data

[63] Continuation of Ser. No. 652,620, Feb. 8, 1991, abandoned.

[30] Foreign Application Priority Data

Feb. 13, 1990 [JP] Japan ............................. 2-31736

[51] Int. Cl.⁶ .................. A61K 7/035; A61K 7/135; A61K 7/48
[52] U.S. Cl. ............................... 424/62; 424/69; 514/844
[58] Field of Search .................. 424/59, 60, 62, 69; 514/844

[56] References Cited

FOREIGN PATENT DOCUMENTS

| 4632678 | 9/1971 | Japan | 424/62 |
| 0134410 | 8/1982 | Japan | 424/62 |
| 143302 | 9/1982 | Japan | 424/62 |
| 0057307 | 4/1983 | Japan | 424/62 |

OTHER PUBLICATIONS

Patent Abstracts of Japan, vol. 13, No. 262. p. 9C608 (1989).
Patent Abstracts of Japan, vol. 13, No. 79, p. 96C571 (1989).

*Primary Examiner*—Dale R. Ore
*Attorney, Agent, or Firm*—Fitzpatrick, Cella, Harper & Scinto

[57] ABSTRACT

Disclosed is a cosmetic composition comprising a glutathione/α-cyclodextrin and/or β-cyclodextrin inclusion complex.

The cosmetic composition of the present invention has the effects of glutathione on the skin and is free of an offensive odor of glutathione.

3 Claims, No Drawings

COMPOSITION CONTAINING INCLUSION COMPLEX OF GLUTATHIONE AND A OR β-CYCLODEXTRINE

This application is a continuation of application Ser. No. 07/652,620, filed Feb. 8, 1991, now abandoned.

BACKGROUND OF THE INVENTION

The present invention relates to a cosmetic composition comprising a glutathione/α-cyclodextrin and/or β-cyclodextrin inclusion complex.

Glutathione is a tripeptide which is present in vivo and is known to play an extremely important role in the maintenance of homeostasis of the living body because of its various physiological activities.

More specifically, many activities of glutathione such as detoxication of poisons and extraneous substances in the living body, protection from radiation injury, inhibition of lipid peroxidation by glutathione peroxidase, and inhibition of melanin pigment formation have been reported [Fragrance Journal, 76, 57–58 (1986), ibid., 82, 63–66 (1987)]. Combined use of glutathione and glutathione peroxidase is known (Japanese Published Unexamined Patent Application No. 47709/89).

There are also many reports on the use of glutathione derivatives as components of cosmetic compositions (Japanese Published Examined Patent Application No. 35417/74 and Japanese Published Unexamined Patent Application Nos. 134410/82, 189296/86 and 267711/88].

Further, it is known to incorporate γ-cyclodextrin into a glutathione-containing composition for its stabilization (Japanese Published Unexamined Patent Application No. 63342/89).

Cosmetic compositions comprising glutathione are generally considered to be difficult of marketing because they generate an offensive odor upon use. Thus, use of various glutathione derivatives in place of glutathione has been studied. However, an inexpensive cosmetic composition having the effects of glutathione and no offensive odor and which is utilizable as a material for cosmetics and fills the natural product-oriented demand has not been developed yet.

SUMMARY OF THE INVENTION

The present invention provides a cosmetic composition comprising a glutathione/α-cyclodextrin and/or β-cyclodextrin inclusion complex and a cosmetically acceptable component. The cosmetic composition has the effects of glutathione on the skin such as a whitening effect and a skin-improving effect and does not generate an offensive odor of glutathione upon use. The present invention also provides a method for masking the odor of glutathione by making a glutathione/α-cyclodextrin and/or β-cyclodextrin inclusion complex by bringing glutathione into contact with α-cyclodextrin and/or β-cyclodextrin.

DETAILED DESCRIPTION OF THE INVENTION

Cyclodextrin (hereinafter referred to as CD) is a non-reducing oligosaccharide having the structural formula $(C_6H_{10}O_5)_n$ in which glucose molecules are bonded through α-1,4-bond to form a ring and n is 6 to 12. Currently, three types of basic CD are industrially manufactured, i.e. α-cyclodextrin (hereinafter referred to as α-CD) having 6 glucose molecules in a ring, β-cyclodextrin (hereinafter referred to as β-CD) having 7 glucose molecules in a ring and γ-cyclodextrin (hereinafter referred to as γ-CD) having 8 glucose molecules in a ring.

In the present invention, α-CD and β-CD can be employed singly or in combination. Their derivatives such as dimethyl-CD, trimethyl-CD and hydroxypropyl-CD can also be used.

For example, commercially available CD such as powdery CELDEX (manufactured by Nippon Food Industry Co., Ltd., Japan), RINGDEX (manufactured by Sanraku Co., Ltd., Japan) and TOYODERIN (manufactured by Toyo Jozo Co., Ltd., Japan) may be used.

In the present invention, α-CD and β-CD are usually used in an amount of 0.5 to 15 parts by weight, preferably 1 to 8 parts by weight, based on 1 part by weight of glutathione. The preventive effect of α-CD and β-CD on generation of an offensive odor from glutathione is little exhibited with an amount of less than 0.5 part by weight; and even when the amount exceeds 15 parts by weight, the effect is not increased.

The glutathione/α-CD and/or β-CD inclusion complex can be prepared in a conventional manner [Fine Chemical, 5–14 (Dec. 1, 1986)].

Examples of the cosmetically acceptable components are emulsifiers, oily substances, moisturizers, fragrances, preservatives, coloring agents, whitening agents, and skin nutrients, which are appropriately employed in the cosmetic composition within the range that can achieve the object of the present invention. Known methods of blending components can be applied to the preparation of the composition. The cosmetically acceptable components may be mixed with glutathione and the resulting mixture may be used to prepare an inclusion complex with α-CD and/or β-CD. For example, in order to enhance a whitening effect or a skin-improving effect, a mixture of glutathione with ascorbic acid or a stabilized ascorbic acid such as ascorbic acid-2-phosphoric acid ester may be used to prepare an inclusion complex with α-CD and/or β-CD.

The cosmetic compositions of the present invention are, for example, a whitening powder, a cleansing powder, a powdery pack which is mixed with water just before use, and a cosmetic composed of powder and liquid or emulsion which are mixed just before use.

The present invention is described below by referring to examples and reference examples.

In the examples and reference examples, the unit % in the compositions stands for per cent by weight.

EXAMPLE 1

| Preparation of whitening powder (a) | |
|---|---|
| (A) D-Mannitol | 55.0 (%) |
| Glucose | 40.1 |
| L-Ascorbic acid-2-phosphoric acid ester magnesium salt | 3.0 |
| Dipotassium glycyrrhizinate | 0.2 |
| Citric acid | 0.4 |
| Methyl paraben | 0.1 |
| Glutathione/β-CD inclusion complex (glutathione:β-CD = 4.6:17 by weight) | 0.2 |
| Polyvinylpyrrolidone | 1.0 |
| (B) Denaturated ethanol | |

The above ingredients (A) were uniformly mixed, and to the mixture was added the ingredient (B) in an amount of based on the mixture of the ingredients (A).

The resulting mixture was kneaded and granulated with a extruding granulator. The alcohol was evaporated with a drier to give a whitening powder.

EXAMPLE 2

| Preparation of cleansing powder (a) | |
| --- | --- |
| Potassium myristate | 10.0 (%) |
| Sodium N-cocoyl-L-glutamate | 30.0 |
| Sucrose laurate | 5.0 |
| Glucose | 54.0 |
| Glutathione/β-CD inclusion complex (glutathione:β-CD = 4.6:17 by weight) | 1.0 |

The above ingredients were uniformly mixed and the mixture was immediately packed in containers to give a cleansing powder.

Reference Example 1

Test on deodorization of glutathione

Glutathione (46.098 mg) was mixed with a suitable amount of each CD shown in Table 1, and each mixture was made up to 10 ml with distilled water and then freeze-dried in a conventional manner. The obtained inclusion complexes of glutathione with respective CD were examined for the degree of offensive odor by organoleptic test by 20 experts at room temperature. For evaluation, the degree of odor was classified into 5 stages, wherein the weakest offensive odor was made 1 and the strongest offensive odor was made 5. The test was carried out by putting a small amount of each inclusion complex on the back of the hand, rubbing it with a finger of the opposite hand, and evaluating its odor.

The results are shown in Table 1 as the average value obtained by dividing the total points by the number of persons.

TABLE 1

| CD | Amount added (mg) | Judgment |
| --- | --- | --- |
| α-CD | 145.95 | 1.2 |
| β-CD | 170.25 | 1.0 |
| γ-CD | 194.55 | 4.0 |
| None | — | 5.0 |

Note: The amount of CD added is 0.015 mol/10 ml.

From the above results, it is apparent that the glutathione/α-CD and glutathione/β-CD inclusion complexes have a remarkable deodorizing effect. Some deodorizing effect was also noted with γ-CD but not sufficient for practical use.

Reference Example 2

Process for preparing the glutathione/β-CD inclusion complex

β-CD (17.0 g) was added to 1 liter of purified water with stirring, and 4.6 g of glutathione was added to the mixture in small portions with continued stirring. The resulting solution was freeze-dried in a conventional manner to give 20.9 g of a glutathione/β-CD inclusion complex.

Reference Example 3

Preparation of whitening powder (b)

A whitening powder was obtained in the same manner as in Example 1 except that 0.0426% of glutathione and 0.1574% of glucose were used instead of 0.2% of the glutathione/β-CD inclusion complex.

Preparation of cleansing powder (b)

A cleansing powder was obtained in the same manner as in Example 2, except that 0.213% of glutathione and 0.787% of glucose were used instead of 1.0% of the glutathione/β-CD inclusion complex.

Comparative Experiment

Whitening powders (a) and (b) and cleansing powders (a) and (b) were respectively examined for the degree of offensive odor by organoleptic test by 20 experts at room temperature. The test was carried out by putting 0.1 g each of the cosmetics on the palm of the hand, adding 2 to 3 ml of purified water thereto, and applying the resulting solution all over the face to make evaluation on the offensive odor smelled upon application.

The results are shown in Table 2.

TABLE 2

| Judgment | — | ± | + |
| --- | --- | --- | --- |
| Whitening powder (a) | 19 | 1 | 0 |
| Whitening powder (b) | 0 | 0 | 20 |
| Cleansing powder (a) | 20 | 0 | 0 |
| Cleansing powder (b) | 0 | 0 | 20 |

Note
—: No offensive odor was noted.
±: Ambiguous
+: Offensive odor was noted.
(Numerals in the table indicate the number of persons)

From the above results, it is apparent that the cosmetic compositions containing the glutathione/β-CD inclusion complex do not generate an offensive odor. Further, the effects of glutathione on the skin were not impaired.

What is claimed is:

1. In an improved skin care or cosmetic composition comprising glutathione, the improvement comprising:
   said composition containing an amount of cyclodextrine sufficient to form an inclusion complex with said glutathione and reduce the odor of said glutathione, wherein said cyclodextrine is at least one of α-cyclodextrine and β-cyclodextrine.

2. A composition according to claim 1, wherein said cyclodextrine is contained in a total amount of 0.5 to 15 parts by weight based on 1 part by weight of glutathione.

3. A composition according to claim 2, wherein said cyclodextrine is contained in a total amount of 1 to 8 parts by weight based on 1 part by weight of glutathione.

* * * * *

UNITED STATES PATENT AND TRADEMARK OFFICE
CERTIFICATE OF CORRECTION

PATENT NO. : 5,407,667

DATED : April 18, 1995

INVENTOR(S): ICHIRO MATSUURA ET AL.  Page 1 of 2

It is certified that error appears in the above-identified patent and that said Letters Patent is hereby corrected as shown below:

```
  On the title page:Item [54]

"A OR" should read --α-OR--.

[56] REFERENCES CITED

Foreign Patent Documents
    "4632678" should read --46-32678--.
    Insert: --JP  63342  1989  Japan .... A23J 3/00--.
    Insert: --EP 0241572 1987  Europe ... A61K 7/42--.
    Insert: --JP  35417  1974  Japan .... A61K 7/00--.
    Insert: --JP  47709  1989  Japan .... A61K 7/00--.
    Insert: --JP 189296  1986  Japan .... A61K 7/00--.
    Insert: --JP 267711  1989  Japan .... A61  7/00--.

Other Publications
    Insert: --Fragrance Journal, Vol. 76, pp. 57-58 (1986)--.
    Insert: --Fragrance Journal, Vol. 82, pp. 65-66 (1987)--.
    Insert: --Fine Chemical, pp. 5-14 (December 1, 1986)--.

COLUMN 1

Line 3, "A OR" should read --α-OR--.
```

UNITED STATES PATENT AND TRADEMARK OFFICE
CERTIFICATE OF CORRECTION

PATENT NO. : 5,407,667

DATED : April 18, 1995

INVENTOR(S) : ICHIRO MATSUURA ET AL.

It is certified that error appears in the above-identified patent and that said Letters Patent is hereby corrected as shown below:

<u>COLUMN 3</u>

```
Line 2, "a" should read --an--.
Line 3, "drier" should read --dryer--.
```

Signed and Sealed this

Tenth Day of November 1998

Attest:

BRUCE LEHMAN

Attesting Officer      Commissioner of Patents and Trademarks